United States Patent [19]

Larson et al.

[11] Patent Number: 5,296,624
[45] Date of Patent: Mar. 22, 1994

[54] PREPARATION OF STERICALLY-HINDERED ORGANOSILANES

[75] Inventors: Gerald L. Larson, Newtown; Barry Arkles, Dresher, both of Pa.

[73] Assignee: Huls America, Inc., Piscataway, N.J.

[21] Appl. No.: 981,805

[22] Filed: Nov. 25, 1992

[51] Int. Cl.$^5$ .............................. C07F 7/08; C07F 7/18
[52] U.S. Cl. ................................... 556/435; 556/465; 556/482; 556/489
[58] Field of Search ................ 556/435, 482, 489, 465

[56] References Cited

U.S. PATENT DOCUMENTS

| | | | |
|---|---|---|---|
| 2,507,512 | 5/1950 | Goodwin | 556/435 |
| 2,507,518 | 5/1950 | Goodwin | 556/435 |
| 2,507,520 | 5/1950 | Goodwin | 556/435 |
| 5,072,012 | 10/1991 | Fujiki et al. | 556/435 |
| 5,075,477 | 12/1991 | Jung et al. | 556/435 |

OTHER PUBLICATIONS

R. F. Cunico, L. Bedell, "The Triisopropylsilyl Group as a Hydroxyl-Protecting Function", J. Org. Chem. 1980, 45, 4797–4798.
P. F. Hudrlik, A. K. Kulkarni, "New Method for the Preparation of t-Butyldimethylsilyl Triflate", Tetrahedron Letters 26 (11), 1389–1390 (1985).
J. L. Glajch, J. J. Kirkland, "Stable, Sterically Protected, Monofunctional-Silane Bonded-Phase Columns for High Performance Liquid Chromatography", LC-GC 8(2), 140–148 (1990).
E. J. Corey, A. Venkateswarlu, "Protection of Hydroxyl Groups as tert-Butyldimethylsilyl Derivatives", J. Am. Chem. Soc. 94/6190-91 (1972).
S. Hanessian, P. Lavallee, "The Preparation and Synthetic Utility of tert-Butyldiphenysilyl Ethers", Can. J. Chem. 53, 2975–2977 (1975).
T. A. Bither, W. H. Knoth, R. V. Lindsey, W. H. Sharkey, "Triakyl- and Triaryl(iso)cyanosilanes", J. Am. Chem. Soc. 80(16), 4151–4153 (1958).

*Primary Examiner*—Paul F. Shaver
*Attorney, Agent, or Firm*—Davis Hoxie Faithfull & Hapgood

[57] ABSTRACT

The invention relates to compositions containing compounds of the structure (I):

$$(R_1)_a(R_2)_b SiX_c \qquad (I)$$

wherein $R_1$ is a neophyl, neohexyl or $(CH_3)_3SiCH_2$— group; $R_2$ is a methyl group; X is a halo group or a saturated, unsaturated, branched, unbranched or cyclic alkoxy group of 1–18 carbon atoms; a is 1 or 2, b is an integer from 0 to 2, and c is an integer from 1 to 3.

20 Claims, No Drawings

PREPARATION OF STERICALLY-HINDERED ORGANOSILANES

BACKGROUND OF THE INVENTION

The invention relates to compounds falling within the following structure (I):

$$(R_1)_a(R_2)_b SiX_c \quad (I)$$

wherein $R_1$ is a neophyl, neohexyl or $(CH_3)_3SiCH_2$— group; $R_2$ is a methyl group; X is a halo group or a saturated, unsaturated, branched, unbranched or cyclic alkoxy group of 1–18 carbon atoms; a is 1 or 2, b is an integer from 0 to 2, and c is an integer from 1 to 3. The neophyl group is a 2-phenyl-2-methylpropyl group, and the neohexyl group is a 3,3-dimethylbutyl group. The X group represents the functionality of the compounds of the invention. Thus, the compounds of the invention include mono- and polyfunctional silanes.

Sterically-hindered organosilanes have been synthesized by a variety of methods, including hydrosilation of sterically-hindered olefins, reaction of organolithium reagents or organomagnesium halides with halo or alkoxysilanes, and by rearrangements of suitably substituted vinylsilanes.

Monofunctional silanes, including halo- or alkoxysilanes, are often used to generate support structures for use in liquid chromatography. The support structures are prepared by coating the surface of a substrate with sterically-hindered silanes, such as the compounds of the present invention. The substrates already include hydrolyzed silica or chromia which have on their surface hydroxyl groups available for reaction with the sterically-protecting silane reagent. The monofunctional silanes form trialkylsilyl ethers on the surface of the substrate. The chromatographic characteristics are generally imparted by the bulky substituent, such as $R_1$ in structure (I).

Such substrates can be generated with polyfunctional silanes as well. When polyfunctional silanes are employed, the silanes generally polymerize with each other along the surface of the substrate in addition to reacting with the substrate, leaving a surface layer which may not be as well-defined as a layer generated from monofunctional silanes. Both types of structures can be useful media for chromatographic separations. The use of polyfunctional silanes can generate support structures with increased resistance against hydrolysis. Silane support structures, generated from compounds such as those of the present invention, can have unique stabilities to hydrogenolytic or organometallic reagents, reducing agents, and basic or acidic reagents. The structures can often be useful as high performance liquid chromatography packings for separating a wide variety of macromolecules, allowing reproducible analysis of mixtures or isolation of purified components.

It is also known that alkoxysilanes, such as those contemplated by structure (I) wherein X is an alkoxy group, can be used as external electron donors in supported Ziegler-Natta catalysts. In J. V. Seppala, M. Harkonen, "Effect of the Structure of External Alkoxysilane Donors on the Polymerization of Propene with High Activity Ziegler-Natta Catalysts", Makromol Chem. 190, 2535–2550 (1989), the authors suggest that in the context of propene polymerization, high performance external donors should have two or three alkoxy groups and relatively large, non-linear hydrocarbon groups. The authors also conclude that effective external donors should not have alkoxy substituents that are larger than the ethoxy group, as with the preferred alkoxy compounds of the present invention.

Sterically-hindered organosilanes, such as those of the present invention, can also be useful as blocking agents for organic synthesis.

SUMMARY OF THE INVENTION

The compounds of the invention include those of the following structure (I):

$$(R_1)_a(R_2)_b SiX_c \quad (I)$$

wherein $R_1$ is a neophyl, neohexyl or $(CH_3)_3SiCH_2$— group; $R_2$ is a methyl group; X is a halo group or a saturated, unsaturated, branched, unbranched or cyclic alkoxy group of 1–18 carbon atoms; a is 1 or 2, b is an integer from 0 to 2, and c is an integer from 1 to 3.

DETAILED DESCRIPTION OF THE INVENTION

As indicated, the compounds of the invention can be defined according to the following structure (I):

$$(R_1)_a(R_2)_b SiX_c \quad (I)$$

wherein $R_1$ is a neophyl, neohexyl or $(CH_3)_3SiCH_2$— group; $R_2$ is a methyl group; X is a halo or a saturated, unsaturated, branched, unbranched or cyclic alkoxy group of 1–18 carbon atoms; a is 1 or 2, b is an integer from 0 to 2, and c is an integer from 1 to 3, such that the valence of Si is always observed as 4. Halo is indicated to represent a halogen group such as a chloro, bromo, iodo or fluoro group. The preferred alkoxy group are the methoxy and ethoxy groups. Table 1 lists certain physical properties of several of the compounds included within structure (I).

TABLE 1

| Compound | b.p. C/mmHg | $nD^{20}$ | d g/ml |
|---|---|---|---|
| $(PhMe_2CCH_2)MeSiCl_2$ | 120°/10 | 1.5148 | 1.13 |
| $(PhMe_2CCH_2)Me_2SiCl$ | 84-6°/1.0 | 1.5054 | 1.03 |
| $(PhMe_2CCH_2)_2Si(OMe)_2$ | 145°/0.15 | 1.5268 | 1.01 |
| $(PhMe_2CCH_2)MeSi(OMe)_2$ | 68°/0.3 | 1.4845 | 0.985 |
| $(PhMe_2CCH_2)MeSi(OEt)_2$ | 82°/0.25 | 1.4761 | 0.956 |
| $Me_3CCH_2CH_2SiCl_3$ | 92-4°/48 | 1.4381 | 1.14 |
| $Me_3CCH_2CH_2Si(OMe)_3$ | 91°/20 | 1.4006 | 0.936 |
| $(Me_3CCH_2CH_2)MeSiCl_2$ | 61°/13 | 1.4356 | 0.989 |
| $(Me_3CCH_2CH_2)MeSi(OMe)_2$ | 78°/14 | 1.4090 | 0.863 |
| $(Me_3CCH_2CH_2)MeSi(OEt)_2$ | 52-5°/1.5 | 1.4101 | 0.863 |
| $Me_3SiCH_2SiCl_3$ | 100°/90 | 1.4451 | 1.10 |
| $Me_3SiCH_2MeSiCl_2$ | 119°/155 | 1.4425 | 1.02 |
| $Me_3SiCH_2MeSi(OMe)_2$ | 117°/157 | 1.4131 | 0.854 |

The compounds of the invention can be made by a variety of known methods. Such methods include reacting the Grignard reagents of 2-phenyl-2-methyl-1-chloropropane, 3,3-dimethyl-1-chlorobutane and trimethylsilylmethyl chloride (i.e. neophylmagnesium chloride, neohexylmagnesium chloride and trimethylsilylmethylmagnesium chloride, respectively) with chlorosilanes to generate novel neophylsilanes, neohexylsilanes and trimethylsilylmethylsilanes falling within the structure (I).

These Grignard reagents are generally prepared by the careful addition of neophyl chloride, neohexyl chloride or trimethylsilylmethyl chloride to a slight excess of magnesium turnings in dry, refluxing tetrahydrofuran (THF) or ether, such as ethyl ether, at room temperature or above and standard pressure under an inert gas atmosphere.

All reactions leading to the compounds of the invention should be carried out under anhydrous conditions under an inert atmosphere. Any suitable inert gas, such as nitrogen, argon or helium, can be used.

Useful chlorosilanes which can be reacted with the Grignard reagents include silicon tetrachloride, methyltrichlorosilane, trichlorosilane, dimethyldichlorosilane, methyldichlorosilane, and other chlorosilanes which will produce a final chemical compound in accord with structure (I). The useful chlorosilanes generally fall within the following structure (II):

$$H_d SiCl_e Z_f \qquad (II)$$

wherein Z is a methyl group or a saturated, unsaturated, branched, unbranched or cyclic alkoxy group of 1-18 carbon atoms; and d is an integer from 0 to 1, e is an integer from 1 to 4, and f is an integer from 0 to 2, such that the valence of Si is always observed as 4.

In preparing the compounds of the invention, the Grignard reagent should be added slowly to the chlorosilane. Where a catalyst is necessary, cuprous cyanide is the preferred catalyst, but other catalysts such as other cyanide derivatives and nitriles can also be used. Cyanide derivatives useful as catalysts in the present invention are disclosed in U.S. Pat. No. 4,650,891, which is incorporated herein by reference. The addition should be at a rate sufficient to maintain a gentle reflux. The preferred amount of catalyst is 1 mole percent. Although a catalyst is generally not necessary in the preparation of the compounds of the invention, cuprous cyanide should be used in the preparation of the neophyl derivatives falling within the structure (I).

The reaction mixture should be allowed to stand after the addition of the Grignard reagent until the reflux ceases. It is preferred to add the Grignard reagent to a stirred solution containing a slight molar excess of chlorosilane, say, a 5% excess. Upon completion of the reaction, as indicated, for example, by gas chromatography, the mixture should be cooled to room temperature. The mixture should then be filtered and the filter cake should be washed with any suitable nonpolar, aprotic solvent, such as ether, THF, hexane or toluene. Hexane is preferred. The filtrate and washings should then be combined and the final silane reaction product can be obtained by distillation. In those reactions involving THF as the solvent, the salts must be removed by either a second filtration after concentration or by adding hexane to extinguish the salts prior to filtration. This is especially true of the neophyl derivatives, which have been found to decompose upon distillation in the presence of magnesium salts.

Useful silanes which can be reacted with the Grignard reagents also include alkoxysilanes. Such alkoxysilanes include those wherein the alkoxy group is a saturated, unsaturated, branched, unbranched or cyclic alkoxy group of 1-18 carbon atoms The methoxy and ethoxy groups are preferred. The alkoxy group can act as a leaving group allowing the addition of the alkyl group from the Grignard reagent. The alkoxysilanes can be prepared by reacting a chlorosilane with the corresponding alkanol. This can be done through the addition of the alkanol to a solution of a chlorosilane in hexane. The mixture should be stirred and purged with an inert gas, such as nitrogen, to remove the hydrogen chloride formed as the reaction proceeds.

Reaction with chloroalkoxysilane can produce a silane with two substituents added from the Grignard reagent and two alkoxy groups. It has been observed that reaction of the Grignard reagents with chloroalkoxysilane may not ensure the presence of two alkoxy groups in the final reaction product. The reaction mixture resulting after the addition of the Grignard reagent should be filtered, and the filter cake washed with a hydrocarbon solvent. The filtrate and washings should then be charged to a reaction vessel along with the corresponding alkanol and sodium alkoxide. The completion of the reaction will be indicated when hydrogen gas ceases to evolve. The reaction product can then be appropriately separated through distillation, as described above.

The compounds of the invention can also be made by reacting the neophylchlorosilanes, neohexylchlorosilanes and trimethylsilylmethylchlorosilanes with alkoxyorthoacetate to make neophylalkoxysilanes, neohexylalkoxysilanes, and trimethylsilylmethylalkoxysilanes. In this process, the orthoacetate should be added slowly to a reaction vessel charged with the silane. Preferably, the amount of orthoacetate added should be at least twice the molar amount of silane present in the reaction vessel. The mildly exothermic reaction mixture should be allowed to stand until the reflux ceases. No solvent or catalyst is necessary. Upon completion of the reaction, as indicated, for example, by gas chromatography, the final silane reaction product can be separated by distillation.

Neohexylchlorosilanes in accord with structure (I) can be made by hydrosilation of neohexene with a chlorosilane under catalysis with chloroplatinic acid. The chloroplatinic acid should be present in the range of from $10^{-3}$ to $10^{-5}$ mol %. The chlorosilane should be of the structure (III)

$$HSiCl_g(CH_3)_h \qquad (III)$$

wherein g is an integer from 1 to 3, and h is an integer from 0 to 2, such that the valence of Si is always observed to be 4. A reaction vessel should be charged with neohexene and chloroplatinic acid in a solvent, such as THF. The mixture should be heated to reflux, and the silane should be added slowly to maintain a moderate reflux. A molar excess of neohexene or the silane is not necessary. When the exothermic reaction mixture ceases to reflux on its own, the final silane reaction product can be obtained by distillation.

The following examples further illustrate the preparation of the compounds of the invention.

EXAMPLE 1

Neophylmagnesium chloride was prepared by the careful addition of 500 g (2.96 mol) of neophyl chloride to 75 g (3.125 mol) of magnesium turnings in 1.25 liters of dry THF. A five liter, 4-necked flask equipped with an overhead stirrer, condenser, thermometer and addition funnel was charged with 387 g (3.125 mol) of dimethyldichlorosilane, 3.0 g of cuprous cyanide and 250 ml of THF. Neophylmagnesium chloride was added dropwise from the addition funnel at such a rate as to maintain a gentle reflux. After the 2 hr. addition and additional 1 hr. reflux the reaction mixture was cooled, filtered and the filter cake was washed with hexane (2×250 ml). The combined organic layers were concentrated at reduced pressure and diluted with 100 ml hexane and again filtered. Reduced pressure concentration and distillation of the product gave 493 g (73% of theory) of neophyldimethylchlorosilane.

EXAMPLE 2

In accord with the procedure of Example 1, neophylmagnesium chloride was prepared from 674 g (4 mol) of neophyl chloride and 105 g (4.4 mol) of magnesium turnings in 1.5 liters of dry THF. The neophylmagnesium chloride was added to 598 g (4 mol) of methyltrichlorosilane and 2 g of cuprous cyanide in 500 ml of THF. 640 g (65% of theory) of neophylmethyldichlorosilane was obtained.

EXAMPLE 3

A 2 liter, 4-necked flask was charged with 68 g (0.5 mol) of trichlorosilane and 100 ml of hexane at 20° C. 40 ml (1.0 mol) of methanol was added to the solution. The reaction mixture was stirred at 25° C. and purged with nitrogen to remove the HCl formed. Cuprous cyanide (2 g) was added and 675 ml of a 1N neophylmagnesium chloride solution in THF was added over a 2 hr. period. The reaction mixture was then refluxed for 6 hr., cooled to 25° C. and filtered. The filter cake was washed with 100 ml of hexane. The combined organic layers were concentrated at reduced pressure and the residue was transferred to a 500 ml, 3-necked flask to which 50 ml of methanol and 5 ml of a 25% solution of sodium methoxide in methanol was added. The reaction mixture was heated to reflux until evolution of $H_2$ was no longer observed. The reaction mixture was then diluted with 200 ml of hexane, washed with cold water (200 ml) and dried over sodium sulfate. Reduced pressure solvent removal and distillation gave 107 g (60% of theory) of dineophyldimethoxysilane.

EXAMPLE 4

A 1 liter, 4-necked flask equipped as in Example 1 was charged with neophylmethyldichlorosilane (200 g, 0.81 mol) and triethylorthoacetate (275 g, 1.7 mol). The reaction mixture was stirred for 16 hrs. Gas chromatographic analysis indicated the reaction was completed. Reduced pressure concentration and distillation gave 205 g (95% of theory) of neophylmethyldiethoxysilane.

EXAMPLE 5

A 500 ml, 3-necked flask fitted with a reflux condenser, a thermometer, and an addition funnel was charged with neophylmethyldichlorosilane. Trimethylorthoacetate was added slowly from the addition funnel. The reaction was mildly exothermic. The contents refluxed overnight. Gas chromatography indicated the completion of the reaction. Upon cooling to room temperature, and distillation under reduced pressure, 181 g (98% of theory) of neophylmethyldimethoxysilane was obtained.

EXAMPLE 6

A 2 liter, 4-necked flask equipped as in Example 1 was charged with 500 g (5.94 mol) of neohexene and 1 ml of a 10% chloroplatinic acid in THF solution. The mixture was heated to reflux (about 42° C.). 805 g (5.94 mol) of methyldichlorosilane was then added dropwise. After the addition of about 70 ml of the silane, the reaction commenced and the temperature in the flask rose to 102° C. as the remainder of the silane was added. The reaction mixture was allowed to cool to room temperature (about 25° C.) after the addition of the silane. Upon completion of the reaction, the remaining volatile components were removed at reduced pressure and the residue was distilled to give 1100 g (84% of theory) of neohexylmethyldichlorosilane.

EXAMPLE 7

A 3-liter, 4-necked flask equipped with an overhead stirrer, condenser, pot thermometer and additional funnel was charged with 970 g (4.49 mol) of 25% sodium methoxide in methanol. To this was added 401 g (2.01 mol) of neohexylmethyldichlorosilane at a rate such as to maintain reflux. Upon completion of the reaction, additional sodium methoxide solution was added to bring the pH to 10. The reaction mixture was cooled to room temperature and 500 ml of hexane was added. The reaction mixture was then filtered and the volatiles removed at 60° C. and 150 mm pressure. The volatiles consisted of two layers. The lower methanol layer was extracted with hexane (2×200 ml) and combined with the original top layer of hexane. The combined hexane layers were distilled through an 18" glass packed column to give 268 g (70% of theory) of neohexylmethyldimethoxysilane. Neohexylmethyldiethoxysilane was prepared following an analogous procedure.

Compounds according to structure (I) wherein X is a halo group other than the chloro group can be prepared, and react in a similar manner, as the compounds of structure (I) wherein X is the chloro group. Further, compounds according to structure (I) wherein X is an alkoxy group other than the methoxy or ethoxy group can be prepared in the same general manner illustrated for the silane compounds containing the methoxy or ethoxy group. The chloro group is preferred where other leaving groups, such as an alkoxy, amino or acetate group, are sought to be added to the silane compound by way of replacement of one or more chloro groups.

What is claimed is:

1. A composition comprising a compound of the structure

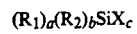

wherein $R_1$ is a neophyl group; $R_2$ is a methyl group; X is a halo group or a saturated, unsaturated, branched, unbranched or cyclic alkoxy group of 1–18 carbon atoms; a is 1 or 2, b is an integer from 0 to 2, and c is an integer from 1 to 3.

2. A composition comprising a compound of the structure

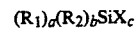

wherein $R_1$ is a neophyl group; $R_2$ is a methyl group; X is a halo group or a saturated, unsaturated, branched, unbranched or cyclic alkoxy group of 1–18 carbon atoms; a is 1 or 2, b is an integer from 0 to 2, and c is an integer from 1 to 3.

3. A composition comprising a compound of the structure

wherein $R_1$ is a $(CH_3)_3SiCH_2$ group; X is a saturated, unsaturated, branched, unbranched or cyclic alkoxy group of 1–18 carbon atoms; a is 1 or 2, and c is 2 or 3.

4. The composition of claim 1 wherein a is 1, b is 2, X is a chloro group and c is 1.

5. The composition of claim 1 wherein a is 1, b is 1, X is a chloro group and c is 2.

6. The composition of claim 1 wherein a is 2, b is 0, X is a methoxy group and c is 2.

7. The composition of claim 1 wherein a is 1, b is 1, X is an ethoxy group and c is 2.

8. The composition of claim 1 wherein a is 1, b is 1, X is a methoxy group and c is 2.

9. The composition of claim 2 wherein a is 1, b is 1, X is a chloro group and c is 2.

10. The composition of claim 2 wherein a is 1, b is 1, X is an ethoxy group and c is 2.

11. The composition of claim 2 wherein a is 1, b is 0, X is a chloro group and c is 3.

12. The composition of claim 2 wherein a is 1, b is 0, X is a methoxy group and c is 3.

13. The composition of claim 2 wherein a is 1, b is 1, X is a methoxy group and c is 2.

14. The composition of claim 3 wherein a is 1, and c is 3.

15. The composition of claim 3 wherein a is 2, and c is 2.

16. The composition of claim 3 wherein a is 2, X is a methoxy group and c is 2.

17. The composition of claim 3 wherein a is 1, X is an ethoxy group and c is 3.

18. The composition of claim 1 wherein X is a chloro group.

19. The composition of claim 2 wherein X is a chloro group.

20. The composition of claim 3 wherein X is an alkoxy group having from 1 to 4 carbon atoms.

* * * * *

UNITED STATES PATENT AND TRADEMARK OFFICE
CERTIFICATE OF CORRECTION

PATENT NO. : 5,296,624

DATED : March 22, 1994

INVENTOR(S) : Gerald L. Larson, et al

It is certified that error appears in the above-identified patent and that said Letters Patent is hereby corrected as shown below:

In claim 2, column 6, line 56, replace "neophyl" with —neohexyl—.

Signed and Sealed this

Sixth Day of September, 1994

*Attest:*

BRUCE LEHMAN

*Attesting Officer*     *Commissioner of Patents and Trademarks*